US011655231B2

United States Patent
Bao et al.

(10) Patent No.: US 11,655,231 B2
(45) Date of Patent: May 23, 2023

(54) ETORICOXIB SOLVATES AND PREPARATION METHOD THEREOF

(71) Applicant: Tianjin University, Tianjin (CN)

(72) Inventors: Ying Bao, Tianjin (CN); Feng Zhang, Tianjin (CN); Peihua Liang, Tianjin (CN); Baohong Hou, Tianjin (CN); Chuang Xie, Tianjin (CN); Ting Zhang, Tianjin (CN); Yinghui Chai, Tianjin (CN)

(73) Assignee: Tianjin University, Tianjin (CN)

( * ) Notice: Subject to any disclaimer, the term of this patent is extended or adjusted under 35 U.S.C. 154(b) by 134 days.

(21) Appl. No.: 17/208,043

(22) Filed: Mar. 22, 2021

(65) Prior Publication Data

US 2021/0300892 A1    Sep. 30, 2021

(30) Foreign Application Priority Data

Mar. 31, 2020 (CN) .......................... 202010244609.9

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; C07B 2200/13
See application file for complete search history.

(56) References Cited

U.S. PATENT DOCUMENTS

| 6,441,002 B1 * | 8/2002 | Clas | ...................... | A61K 31/444 |
| | | | | 514/334 |
| 7,790,905 B2 * | 9/2010 | Tawa | ................... | C07D 495/04 |
| | | | | 548/375.1 |

FOREIGN PATENT DOCUMENTS

WO    WO-2012163839 A1 * 12/2012    ........... A61K 9/2009

OTHER PUBLICATIONS

D. Ahuja, P. Bannigan, A. Rasmuson, Study of three solvates of sulfamethazine CrystEngComm, 2017,19, 6481-6488. (Year: 2017).*
Dmitry V. Matyushov, Roland Schmid, and Branka M. Ladanyi, The Journal of Physical Chemistry B 1997 101 (6), 1035-1050 DOI: 10.1021/jp961609i (Year: 1997).*

* cited by examiner

*Primary Examiner* — Brandon J Fetterolf
*Assistant Examiner* — Manahil Mirghani Ali Abdalhameed
(74) *Attorney, Agent, or Firm* — MagStone Law, LLP; Enshan Hong

(57) ABSTRACT

The disclosure relates to etoricoxib solvates and a preparation method thereof. A solvent is a hydrogen bond donor solvent with a polarity value π* ranging from 60 to 100 or a hydrogen bond acceptor solvent with a polarity value π* ranging from 92 to 100. Solvents with a polarity value π* within the above range all can form corresponding etoricoxib solvates with etoricoxib. The etoricoxib solvate can be prepared by cooling crystallization or suspension crystallization. A 1,2-propanediol solvate of etoricoxib and a dimethyl sulfoxide (DMSO) solvate of etoricoxib provided in the present disclosure have high thermal stability, unique crystal form, large size, concentrated distribution, and prominent flowability and is safe, pharmaceutically acceptable, and not easy to agglomerate. Compared with etoricoxib, the etoricoxib solvates exhibit significantly improved solubility. Moreover, preparation of the solvates requires low consumption in time, energy, and solvent, and has high efficiency, with a molar yield higher than 90%.

5 Claims, 7 Drawing Sheets

ETORICOXIB SOLVATES AND PREPARATION METHOD THEREOF

RELATED APPLICATIONS

This application claims the priority from China Patent Application Serial Number 202010244609.9, filed on Mar. 31, 2020, the content of which is incorporated here by reference.

BACKGROUND OF THE INVENTION

1. Technical Field

The present disclosure belongs to the technical field of chemical engineering crystallization and relates to etoricoxib solvates and a preparation method thereof.

2. Description of the Related Art Background

Etoricoxib has a chemical name of 5-chloro-6'-methyl-3-[4-(methylsulfonyl)phenyl]-2,3'-bipyridine, a molecular formula of $C_{18}H_{15}ClN_2O_2S$, a relative molecular weight of 358.84, and a structural formula as follows:

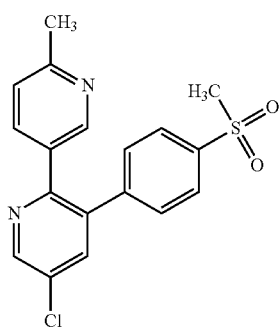 [SMILES: Cc1ccc(-c2ncc(Cl)cc2-c2ccc(S(C)(=O)=O)cc2)cn1]

Etoricoxib is a selective cyclooxygenase-2 (COX-2) non-steroidal anti-inflammatory drug (NSAID), which is commonly used in the treatment of osteoarthritis (OA), rheumatoid arthritis (RA), and acute gouty arthritis (AGA). As an oral drug, etoricoxib has lower gastrointestinal toxicity than traditional NSAIDs.

The crystals of etoricoxib have multiple crystal forms. U.S. Pat. No. 6,441,002B1 discloses etoricoxib crystal forms I, II, III and IV, hemihydrate, sesquihydrate, and amorphous form, and preparation methods thereof. Patent WO02096877A1 discloses an etoricoxib crystal form V and a preparation method thereof. Powder X-ray diffraction (PXRD) characterization and thermal analysis parameters for these crystal forms are shown in Table 1.

TABLE 1

| | PXRD characteristic peak positions, melting points, and enthalpies of fusion of different etoricoxib crystal forms | | |
|---|---|---|---|
| Crystal form | PXRD characteristic peak position 2θ (°) | Melting point (° C.) | Enthalpy of fusion (kJ/mol) |
| I | 7.1, 9.7, 11.8, 15.5, 20.1, 22.7, 24.1 | 134.0 ± 0.6 | 27.2 ± 0.9 |
| II | 5.6, 9.4, 10.7, 17.6 | 131.0 ± 1 | 25.8 ± 0.2 |
| III | 10.5, 16.1, 22.4 | 133 | 22.7 |
| IV | 8.7, 15.2, 17.1, 19.5, 21.7, 23.5, 23.6 | 134.0 ± 0.1 | 27.9 ± 0.2 |
| V | 4.2, 4.5, 4.7, 4.8, 4.9, 5.0, 5.7, 5.8, 6.7, 6.9, 7.2, 13.7 | 133.9 | 24.8 |
| Amorphous form | no characteristic peak | no definite melting point | / |
| Hemihydrate | 8.6, 14.8, 15.9, 16.3, 17.4, 18.1, 20.0, 21.9, 24.0 | an onset temperature of dehydration is lower than 56° C. | / |
| Sesquihydrate | 7.1, 9.7, 11.8, 15.5, 20.1, 22.7, 24.1 | an onset temperature of dehydration is lower than 23° C. | / |

Among these crystal forms of etoricoxib, the crystal form I is a kinetic dominant crystal form, which is the easiest to crystallize from a solution. U.S. Pat. No. 6,441,002B1 discloses the etoricoxib crystal form I and a preparation method thereof. The crystal form I is obtained by subjecting crystal form II in a mixed solvent of isopropanol and n-hexane to suspension crystallization, which is needle-like, small in bulk density, small in size, and easy to agglomerate. Moreover, the crystal form is metastable at room temperature, so there is a hidden danger of crystal form transformation during storage and transportation.

Etoricoxib crystal form V is a stable crystal form at room temperature and is also a crystal form used in the pharmaceutical preparation. Patent WO02096877A1 discloses the etoricoxib crystal form V and a preparation method thereof. The preparation method of the crystal form is as follows: dissolving the crystal form I, II, III or IV in isopropyl acetate, heating a resulting solution to about 75° C., and conducting cooling crystallization to obtain the crystal form V with crystal habits of parallelogram-shaped blocks. In an actual production process, this method is likely to cause an impure crystal form as the crystal form I is easily formed due to explosive nucleation caused by excessive local supersaturation, and high supersaturation will also make a crystal product have small size, wide size distribution, and easy to aggregate, and other issues. Patent CN108069896A discloses a method for preparing crystal form V by adding a seed crystal, including: preparing a 75° C. etoricoxib solution using any one of isopropyl acetate, ethyl acetate, and acetone or any mixed solvent of two or more thereof, adding 3% to 10% of crystal form V as a seed crystal, and conducting cooling crystallization at a cooling rate not higher than 20° C./min to obtain the crystal form V. This method still does not solve the problem that the crystal form I is easily formed due to explosive nucleation caused by excessive local supersaturation, which greatly limits the industrial application of this method. Patent CN107056691A discloses a method for inducing the crystallization of crystal form V by adding formic acid, acetic acid, sulfuric acid, etc. during a cooling crystallization process. This method strongly depends on an acid addition amount and a cooling rate, and a residual toxic acid in a crystal product will greatly affect the medicinal safety of the product.

U.S. Pat. No. 6,441,002B1 discloses a method for preparing a hemihydrate. A hemihydrate with block-like shape is obtained by suspending the etoricoxib crystal form IV in water for more than 1 d, which is time-consuming. At a high humidity, a hemihydrate will be transformed into a sesquihydrate. The hemihydrate has an onset temperature of dehydration lower than 56° C., and the sesquihydrate has an onset temperature of dehydration lower than 23° C. Both of the two will be transformed into the crystal form I after dehydration. Therefore, the two hydrates of etoricoxib have poor thermal stability, which is not conducive to the storage and transportation of drugs and will also result in an impure drug crystal form due to crystal form transformation.

There are mainly three problems in the prior art. (1). The two hydrates of etoricoxib have poor thermal stability, indicating that there is a weak intermolecular interaction between water and etoricoxib, and it is difficult to avoid the problem of poor thermal stability in the development of new hydrate crystal forms. (2). The pharmaceutical etoricoxib crystal form V is impure in crystal form, small in size, non-concentrated in size distribution, and easy to aggregate, which greatly affects the subsequent processing efficiency, drug quality, and efficacy. (3). Studies in references (DOI: 10.1021/acs.jced.5b00201 and DOI: 10.1021/acs.jced.7b00709) have shown that various unsolvated crystal forms of etoricoxib have an extremely low solubility in an aqueous solution, which is a major factor that limits the clinical therapeutic effect of the drug. A molecular structure determines the lipophilicity and hydrophobicity of etoricoxib, so it is difficult to significantly improve the solubility by developing new unsolvated crystal forms of etoricoxib.

A drug may have changed physical properties due to the introduction of solvent molecules into its crystal structure. Therefore, developing solvates is a technical approach to improve the solubility and performance of a drug. Moreover, the molecular structure of etoricoxib lacks typical hydrogen bond donors, so hydrogen bond donors and hydrogen bond acceptors are out of balance in the structure. It is considered that the introduction of suitable solvent molecules is likely to cause the formation of an etoricoxib solvate due to the spontaneous balance tendency of hydrogen bond donors and acceptors in the system. However, developing new solvates usually requires a large number of solvent screening experiments, leading to heavy workload, low efficiency, and long experimental period. Therefore, it is necessary to develop solvent selection and preparation methods for etoricoxib solvates. A solvent is efficiently selected to prepare a new safe and medicinal etoricoxib solvate with high stability, unique crystal form, large size, narrow size distribution, and prominent flowability by a simple preparation method, with high yield, low energy consumption, and low solvent consumption. More importantly, an obtained solvate has significantly improved solubility compared with unsolvated forms.

SUMMARY OF THE INVENTION

In order to solve the problems in the prior art, research and exploration is conducted. The formation of solvates is mainly driven by the following two mechanisms: (1) Solvent molecules can form a strong electrostatic interaction with drug molecules to improve the electrostatic potential imbalance of drug molecules; and (2) Solvent molecules fill voids in crystal structure through weak van der Waals interaction to improve the packing efficiency of crystal structure. Etoricoxib is a drug that lacks typical hydrogen bond donors, and there are polar functional groups such as methylpyridine ring, chloropyridine ring, and methylsulfonyl in its molecular structure. Analysis of molecular surface electrostatic potential shows that polar functional groups on an etoricoxib molecule exhibit a strong imbalanced electrostatic potential distribution. Negatively charged active sites are mainly located on an N atom of a pyridine ring and O atoms of sulfonyl, while positively charged active sites are mainly located on methyl of sulfonyl. There is also a strong imbalanced electrostatic potential distribution in hydrogen bond donor and acceptor solvent molecules with a relatively-strong polarity themselves. Therefore, the electrostatic complementarity (EC) between host and guest molecules has become a decisive factor for the formation of a corresponding solvate of etoricoxib. Moreover, hydrogen bond donor solvent molecules with high polarity tend to form solvated dimers with N on a methylpyridine ring based on EC, while hydrogen bond acceptor solvent molecules with high polarity tend to form solvated dimers with a methylsulfonyl moiety based on EC. These dimers further assemble into a solvate through the strong electrostatic interaction among molecules. Quantum chemical calculations focusing on solvent molecules show that the electrostatic interaction between solvent molecules and surrounding molecules in a crystal structure decreases with the decrease of solvent polarity. When hydrogen bond donor solvents have a polarity value $\pi^*$ ranging from 60 to 100, or when hydrogen bond acceptor solvents have a polarity value $\pi^*$ ranging from 92 to 100, there is an electrostatic contribution close to or higher than 50% between solvent molecules and surrounding molecules in a crystal structure, indicating that the strong electrostatic interaction between solvent molecules and surrounding molecules allows solvent molecules to easily enter crystal lattices, thus forming a solvate. Detailed calculation results are shown in FIG. 1. When hydrogen bond donor solvents have a polarity value $\pi^*$ lower than 60, or when hydrogen bond acceptor solvents have a polarity value $\pi^*$ lower than 92, there is an electrostatic contribution much lower than 50% between solvent molecules and surrounding molecules, indicating that the interaction between solvent molecules and surrounding molecules in a crystal structure is dominated by weak van der Waals interaction. Since the interaction between solvent molecules and surrounding molecules is too weak to maintain a stable crystal structure, these solvents cannot enter crystal lattices to form solvates with etoricoxib. In addition, the applicants conduct a systematic etoricoxib solvate screening experiment on 22 kinds of solvents with different polarities, and experimental results are in agreement with conclusions of the above theoretical calculations. Hydrogen bond donor solvents with a polarity value π* ranging from 60 to 100 or hydrogen bond acceptor solvents with a polarity value π* ranging from 92 to 100 can form solvates with etoricoxib.

The present disclosure proposes a new technical solution based on the above calculation and experimental results and discloses etoricoxib solvates and a preparation method thereof.

The present disclosure discloses an etoricoxib solvate, and a solvent is a hydrogen bond donor solvent with a polarity value π* ranging from 60 to 100 or a hydrogen bond acceptor solvent with a polarity value π* ranging from 92 to 100. Solvents with a polarity value π* within the above range all can form corresponding etoricoxib solvates with etoricoxib.

The hydrogen bond donor solvent with a polarity value π* ranging from 60 to 100 may include: methanol with a polarity value π*=60, 1,2-propanediol with a polarity value π*=85, ethylene glycol (EG) with a polarity value π*=92, and formamide with a polarity value π*=97.

The hydrogen bond acceptor solvent with a polarity value π* ranging from 92 to 100 may include: N-methylpyrrolidone (NMP) with a polarity value π*=92 and dimethyl sulfoxide (DMSO) with a polarity value π*=100.

The etoricoxib solvates may include a methanol solvate of etoricoxib, a 1,2-propanediol solvate of etoricoxib, an EG solvate of etoricoxib, a formamide solvate of etoricoxib, an NMP solvate of etoricoxib, and a DMSO solvate of etoricoxib. PXRD and TGA/DSC results of these 6 etoricoxib solvates are shown in FIG. 2 and FIG. 3, respectively, and detailed characteristic parameters of each solvate are shown in Table 2.

In the present disclosure, PXRD test conditions are as follows: Rigaku D/max 2500 X-ray powder diffractometer; CuKα radiation; tube voltage: 40 kV; filament current: 100 mA; continuous scanning; step size: 0.02°; scanning speed: 8°/min; and scanning range: 2° to 40°.

TGA data of all solvates in the present disclosure are determined by a thermogravimetric analyzer (Mettler Toledo TGA/DSC 1/SF, Mettler Toledo, Switzerland), and analysis conditions are as follows: 5 mg to 10 mg of a sample in a 70 μL ceramic crucible; reaction gas and protective gas: high-purity nitrogen; flow rates: 50 mL/min and 20 mL/min; heating rate: 10° C./min; and temperature range: 25° C. to 250° C. DSC data are determined by a differential scanning calorimeter (DSC1/500, Mettler Toledo, Switzerland), and analysis conditions are as follows: 5 mg to 10 mg of a sample in a 40 μL aluminum crucible; reaction gas and protective gas: high-purity nitrogen; flow rates: 50 mL/min and 20 mL/min; heating rate: 10° C./min; and temperature range: 25° C. to 250° C.

1 mol of the methanol solvate of etoricoxib according to the present disclosure includes 1 mol of methanol, and the methanol solvate of etoricoxib has a structural formula shown in (I).

The methanol solvate of etoricoxib according to the present disclosure has the following characteristics: monoclinic crystal system; space group: P2/c; unit cell parameters: a=13.5993 Å, b=10.0612 Å, c=15.1833 Å, α=90°, β=113.50°, and γ=90'; and unit cell volume: 1905.08 Å$^3$. In the crystal structure, each unit cell includes 4 etoricoxib molecules and 4 methanol molecules, and the molecular packing and asymmetric unit structure are shown in FIG. 4.

TABLE 2

PXRD characteristic peak positions, desolvation temperatures, and thermal weight losses of the 6 etoricoxib solvates disclosed in the present disclosure

| Name of etoricoxib solvates | Solvent polarity value π* | PXRD main characteristic peak position (diffraction angle 2θ, °) | Onset temperature of desolvation in TG test (° C.) | weight loss percentage in TG test (%) |
|---|---|---|---|---|
| Methanol solvate | 60 | 7.08 ± 0.1, 11.48 ± 0.1, 11.82 ± 0.1, 14.28 ± 0.1, 14.74 ± 0.1, 15.46 ± 0.1, 16.72 ± 0.1, 17.24 ± 0.1, 17.62 ± 0.1, 18.74 ± 0.1, 21.36 ± 0.1, 21.78 ± 0.1, 22.60 ± 0.1, 23.10 ± 0.1, 23.78 ± 0.1, 24.48 ± 0.1, 25.56 ± 0.1, 26.10 ± 0.1 | 27 ± 1 | 8.0 |
| 1,2-propanediol solvate | 85 | 9.66 ± 0.1, 11.70 ± 0.1, 14.06 ± 0.1, 15.84 ± 0.1, 16.44 ± 0.1, 17.46 ± 0.1, 18.04 ± 0.1, 23.14 ± 0.1, 23.58 ± 0.1, 24.10 ± 0.1, 25.70 ± 0.1, 26.06 ± 0.1, 27.12 ± 0.1, 29.02 ± 0.1, 30.52 ± 0.1, 32.96 ± 0.1, 33.22 ± 0.1, 38.16 ± 0.1 | 94 ± 1 | 9.4 |
| EG solvate | 92 | 9.62 ± 0.1, 14.44 ± 0.1, 16.16 ± 0.1, 17.56 ± 0.1, 19.50 ± 0.1, 22.12 ± 0.1, 22.45 ± 0.1, 22.76 ± 0.1, 23.30 ± 0.1, 24.98 ± 0.1, 26.04 ± 0.1, 27.10 ± 0.1, 27.84 ± 0.1 | 96 ± 1 | 8.0 |
| Formamide solvate | 97 | 11.26 ± 0.1, 13.02 ± 0.1, 14.24 ± 0.1, 14.72 ± 0.1, 15.56 ± 0.1, 16.58 ± 0.1, 17.00 ± 0.1, 17.18 ± 0.1, 18.20 ± 0.1, 18.44 ± 0.1, 19.22 ± 0.1, 19.86 ± 0.1, 20.52 ± 0.1, 22.64 ± 0.1, 22.98 ± 0.1, 24.28 ± 0.1, 25.62 ± 0.1, 26.04 ± 0.1, 26.20 ± 0.1, 27.58 ± 0.1, 28.70 ± 0.1, 29.68 ± 0.1, 30.28 ± 0.1 | 90 ± 1 | 11.0 |
| DMSO solvate | 100 | 10.87 ± 0.1, 12.14 ± 0.1, 12.66 ± 0.1, 14.58 ± 0.1, 17.34 ± 0.1, 17.80 ± 0.1, 18.08 ± 0.1, 19.08 ± 0.1, 21.13 ± 0.1, 22.00 ± 0.1, 22.28 ± 0.1, 23.44 ± 0.1, 24.24 ± 0.1, 25.00 ± 0.1, 25.46 ± 0.1, 26.14 ± 0.1, 29.42 ± 0.1, 30.38 ± 0.1 | 66 ± 1 | 18.4 |
| NMP solvate | 92 | 8.42 ± 0.1, 10.02 ± 0.1, 15.26 ± 0.1, 15.72 ± 0.1, 16.92 ± 0.1, 17.98 ± 0.1, 18.22 ± 0.1, 19.04 ± 0.1, 19.92 ± 0.1, 20.38 ± 0.1, 20.80 ± 0.1, 21.80 ± 0.1, 22.88 ± 0.1, 23.68 ± 0.1, 24.06 ± 0.1, 24.36 ± 0.1, 24.90 ± 0.1, 25.74 ± 0.1 | 79 ± 1 | 21.0 |

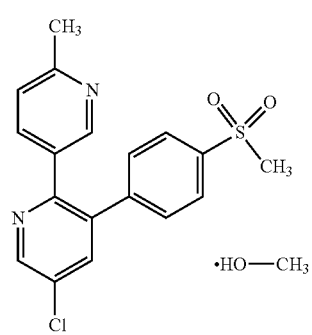

(I)

1 mol of the 1,2-propanediol solvate of etoricoxib according to the present disclosure includes 0.5 mol of 1,2-propanediol, and the 1,2-propanediol solvate of etoricoxib has a structural formula shown in (II).

The 1,2-propanediol solvate of etoricoxib according to the present disclosure has the following characteristics: monoclinic crystal system; space group: C 2/c; unit cell parameters: a=21.731 Å, b=8.2933 Å, c=22.716 Å, α=90°, β=110.90°, and γ=90°; and unit cell volume: 3824.72 Å³. In the crystal structure, each unit cell includes 8 etoricoxib molecules and 4 1,2-propanediol molecules, and the molecular packing and asymmetric unit structure are shown in FIG. 5.

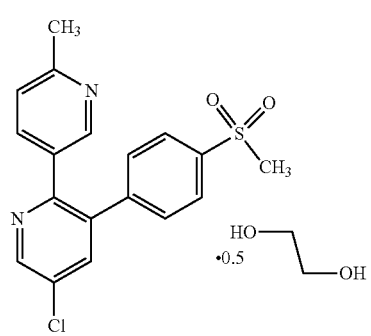

(III)

1 mol of the formamide solvate of etoricoxib according to the present disclosure includes 1 mol of formamide, and the formamide solvate of etoricoxib has a structural formula shown in (IV).

The formamide solvate of etoricoxib according to the present disclosure has the following characteristics: monoclinic crystal system; space group: P2/c; unit cell parameters: a=13.6203 Å, b=10.4282 Å, c=14.8913 Å, α=90°, β=114.11°, and γ=90'; and unit cell volume: 1930.58 Å³. In the crystal structure, each unit cell includes 4 etoricoxib molecules and 4 formamide molecules, and the molecular packing and asymmetric unit structure are shown in FIG. 7.

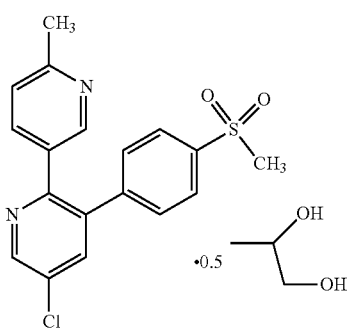

(II)

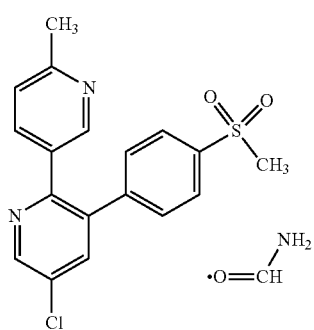

(IV)

1 mol of the EG solvate of etoricoxib according to the present disclosure includes 0.5 mol of EG, and the EG solvate of etoricoxib has a structural formula shown in (III).

The EG solvate of etoricoxib according to the present disclosure has the following characteristics: monoclinic crystal system; space group: P2₁/n; unit cell parameters: a=12.1502 Å, b=8.24082 Å, c=18.3654 Å, α=90°, β=90.45°, and γ=90°; and unit cell volume: 1838.76 Å³. In the crystal structure, each unit cell includes 4 etoricoxib molecules and 4 EG molecules, and the molecular packing and asymmetric unit structure are shown in FIG. 6.

1 mol of the DMSO solvate of etoricoxib according to the present disclosure includes 1 mol of DMSO, and the DMSO solvate of etoricoxib has a structural formula shown in (V).

The DMSO solvate of etoricoxib according to the present disclosure has the following characteristics: triclinic crystal system; space group: P-1; unit cell parameters: a=8.3464 (17) Å, b=8.8665(18) Å, c=15.210(3) Å, α=99.04°, β=100.16°, and γ=108.93°; and unit cell volume: 1019.87 Å³. In the crystal structure, each unit cell includes 2 etoricoxib molecules and 2 DMSO molecules, and the molecular packing and asymmetric unit structure are shown in FIG. 8.

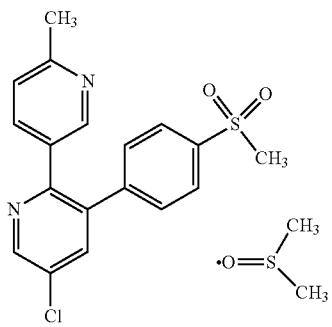

(V)

1 mol of the NMP solvate of etoricoxib according to the present disclosure includes 1 mol of NMP, and the NMP solvate of etoricoxib has a structural formula shown in (VI).

The NMP solvate of etoricoxib according to the present disclosure has the following characteristics: triclinic crystal system; space group: P-1; unit cell parameters: a=9.0649 (18)Å, b=10.924(2)Å, c=11.964(2)Å, α=76.38°, β=84.23° and γ=79.82°; and unit cell volume: 1131.24 Å$^3$. In the crystal structure, each unit cell includes 2 etoricoxib molecules and 2 NMP molecules, and the molecular packing and asymmetric unit structure are shown in FIG. 9.

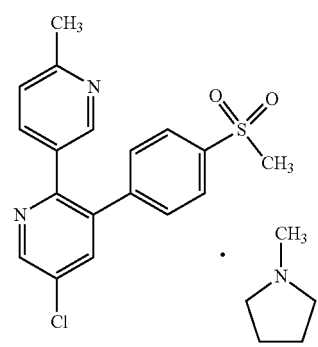

(VI)

In a method for preparing an etoricoxib solvate using a solvent selected from a solvent range for etoricoxib solvates disclosed in the present disclosure, cooling crystallization or suspension crystallization can be adopted.

A preparation method of the etoricoxib solvate according to the present disclosure where cooling crystallization is adopted specifically includes the following steps:

1) adding a raw material of etoricoxib to a solvent, and heating a resulting suspension to 50° C. to 80° C. to obtain a clear solution, where, the etoricoxib and the solvent have a molar ratio of 1:10 to 1:30;

2) cooling the clear solution to 0° C. to 20° C. at a cooling rate of 0.5° C./min to 2° C./min and holding the temperature for 1 h to 5 h; and 3) filtering a resulting suspension after the cooling crystallization is completed, and drying an obtained filter cake under vacuum at 20° C. to 60° C. to obtain a corresponding etoricoxib solvate.

A preparation method of the etoricoxib solvate according to the present disclosure where suspension crystallization is adopted specifically includes the following steps:

1) adding a raw material of etoricoxib to a solvent to obtain a suspension, where, the etoricoxib and the solvent have a molar ratio of 1:10 to 1:30;

2) stirring the suspension at a constant temperature of 15° C. to 40° C. for 1 h to 5 h; and 3) filtering a resulting suspension after the stirring is completed, and drying an obtained filter cake under vacuum at 20° C. to 60° C. to obtain a corresponding etoricoxib solvate.

In the preparation method of etoricoxib solvates using cooling crystallization or suspension crystallization according to the present disclosure, the raw material of etoricoxib may include one of etoricoxib amorphous form, crystal form I, crystal form II, crystal form III, crystal form IV, crystal form V, and hemihydrate, or a mixture of two or more thereof.

The present disclosure provides 6 new etoricoxib solvates. The used solvents of DMSO and 1,2-propanediol have been listed in Generally Recognized as Safe (GRAS) by FDA, which are safe and non-toxic, have no solvent residue limits, and are widely used as solvents for injection and non-injection pharmaceutical preparations and for intramuscular and intravenous injections. In addition, the 1,2-propanediol and DMSO solvates of etoricoxib prepared in the present disclosure have unique crystal form, large crystal size, excellent flowability, no agglomeration, and concentrated size distribution. The preparation process where a filter cake obtained does not need to be washed has low time consumption, high efficiency, and a molar yield higher than 90%. Therefore, the present disclosure effectively solves the problems of uncontrollable crystallization process of etoricoxib, small crystal size, impure crystal form, and so on.

The 1,2-propanediol and DMSO solvates of etoricoxib obtained in the present disclosure are rod-like and bulk crystals, respectively, as shown in FIG. 10 and FIG. 11. The etoricoxib crystal form V in the prior art has a volume-average size of 16 μm and a repose angle of 44°; and the etoricoxib hemihydrate has a volume-average size of 19 μm and a repose angle of 48°. The 1,2-propanediol solvate of etoricoxib obtained in the present disclosure has a primary crystal size of 100 μm and a repose angle of 33° to 35°, and the DMSO solvate has a volume-average size of 120 μm and a repose angle of 22° to 26°, exhibiting significantly improved crystal sizes and particle flowability. The etoricoxib crystal form V and hemihydrate have wide size distributions, with variation coefficients of 57.2% and 53.6%, respectively. The 1,2-propanediol and DMSO solvates of etoricoxib obtained in the present disclosure have relatively concentrated size distributions, with variation coefficients of 23.6% and 19.7%, respectively. Therefore, the 1,2-propanediol and DMSO solvates of etoricoxib obtained in the present disclosure are perfect crystals with smooth surfaces, which are not easy to agglomerate and have prominent flowability. Compared with commercially available etoricoxib products, the solvates have significantly improved crystal habits.

The 1,2-propanediol and DMSO solvates of etoricoxib obtained in the present disclosure have a relatively high desolvation temperature. The 1,2-propanediol and the DMSO have boiling points of 197.3° C. and 189° C., respectively. As the solvents have a high boiling point, the 1,2-propanediol and DMSO solvates of etoricoxib, when stored at room temperature, exhibit excellent thermal stability and will not undergo desolvation and crystal form transformation. Moreover, the host-guest intermolecular interaction energies in the crystal structure of etoricoxib 1,2-propanediol and DMSO solvates are −37.22 kJ/mol and −43.37 kJ/mol respectively, which are much higher than that (−30.53 kJ/mol) in hemihydrate crystal structure. It is difficult for water molecules to enter a unit cell of the 1,2- propanediol and DMSO solvates to replace the 1,2-propanediol and DMSO molecules at an ambient temperature. Therefore, the 1,2-propanediol and DMSO solvates of etoricoxib have prominent moisture stability and both will not be transformed into a hydrate. As a result, the 1,2-propanediol and DMSO solvates of etoricoxib obtained in the present disclosure both have prominent thermal stability and moisture stability.

According to experiments of the present disclosure, the 1,2-propanediol and DMSO solvates of etoricoxib have solubilities of 0.527 g/L and 1.465 g/L in a 25° C. aqueous solution, respectively, while the etoricoxib crystal form V has a solubility only of 0.3079 g/L in an aqueous solution. Therefore, the 1,2-propanediol and DMSO solvates of etoricoxib obtained in the present disclosure both effectively improve the solubility of etoricoxib in an aqueous solution.

The present disclosure provides etoricoxib solvates and a preparation method thereof, where, obtained 1,2-propanediol and DMSO solvates of etoricoxib have important medicinal values and are expected to become effective substitutes for current commercially available crystal form V.

DETAILED DESCRIPTION OF PREFERRED EMBODIMENTS

The above-mentioned content of the present disclosure will be further described in detail below through specific implementations in the form of examples, but it should be understood that a scope of the above-mentioned subject of the present disclosure is not limited to the following examples. Corresponding replacements or modifications can be made based on common technical knowledge and conventional means in the art without departing from the above-mentioned technology of the present disclosure, and the replacements or modifications are all included in the present disclosure.

Example 1

Methanol with a polarity value $\pi^*=60$, 1,2-propanediol with a polarity value $\pi^*=85$, EG with a polarity value $\pi^*=92$, and formamide with a polarity value $\pi^*=97$ were selected from hydrogen bond donor solvents with a polarity value $\pi^*$ ranging from 60 to 100, and crystallization of etoricoxib was conducted in these solvents separately to obtain corresponding methanol, 1,2-propanediol, EG and formamide solvates of etoricoxib.

NMP with a polarity value $\pi^*=92$ and DMSO with a polarity value $\pi^*=100$ were selected from hydrogen bond acceptor solvents with a polarity value $\pi^*$ ranging from 92 to 100, and crystallization of etoricoxib was conducted in the two solvents separately to obtain corresponding NMP and DMSO solvates of etoricoxib.

Figure 1:
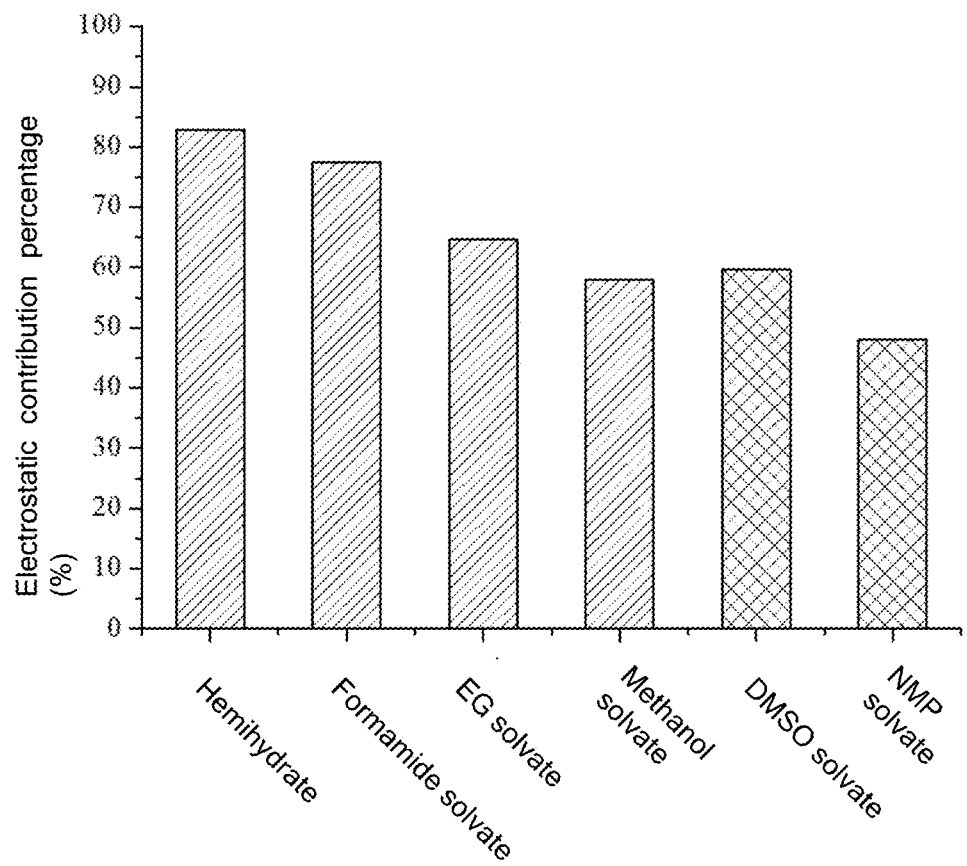
FIG. 1 is a bar chart illustrating electrostatic contribution of the interaction between solvent molecules and etoricoxib molecules.
Figure 2:
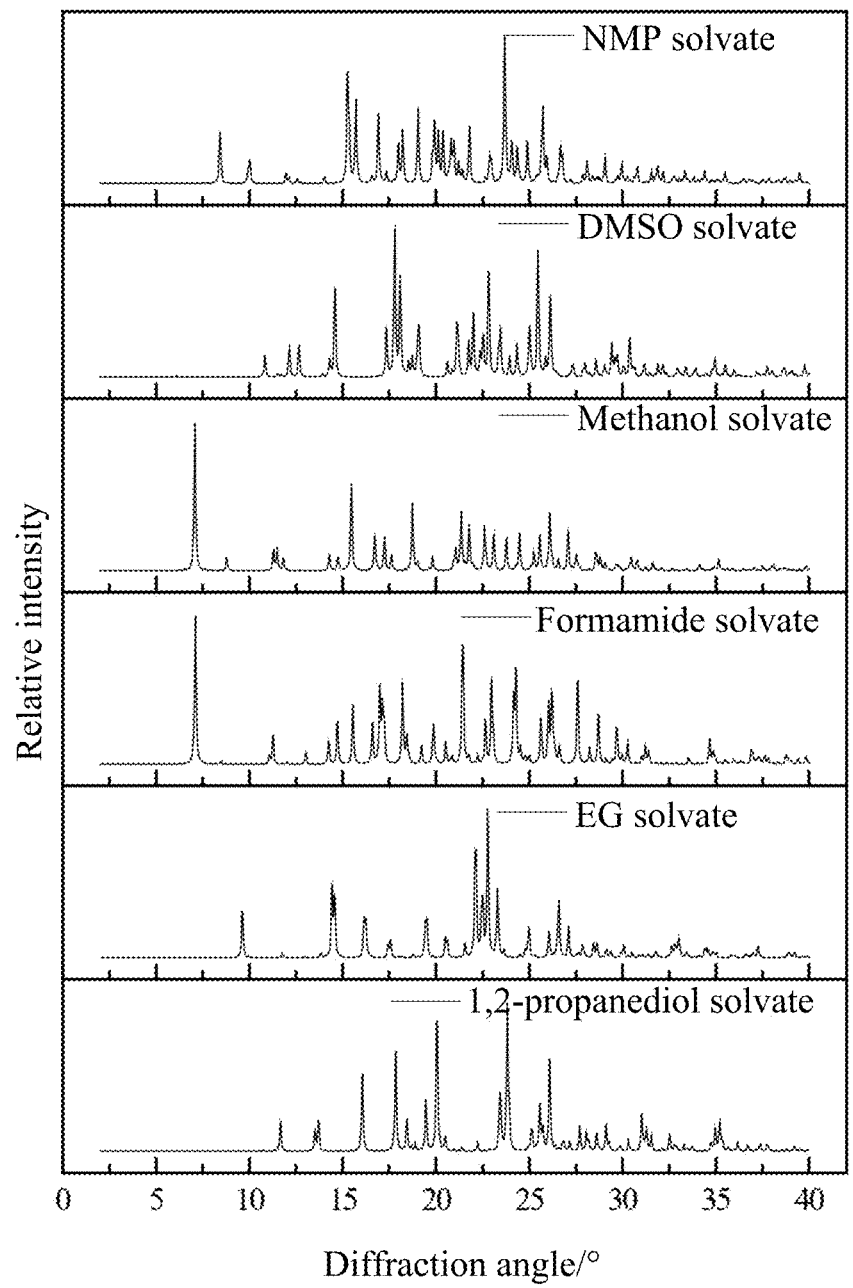
FIG. 2 shows PXRD patterns of the 6 etoricoxib solvates.
Figure 3:
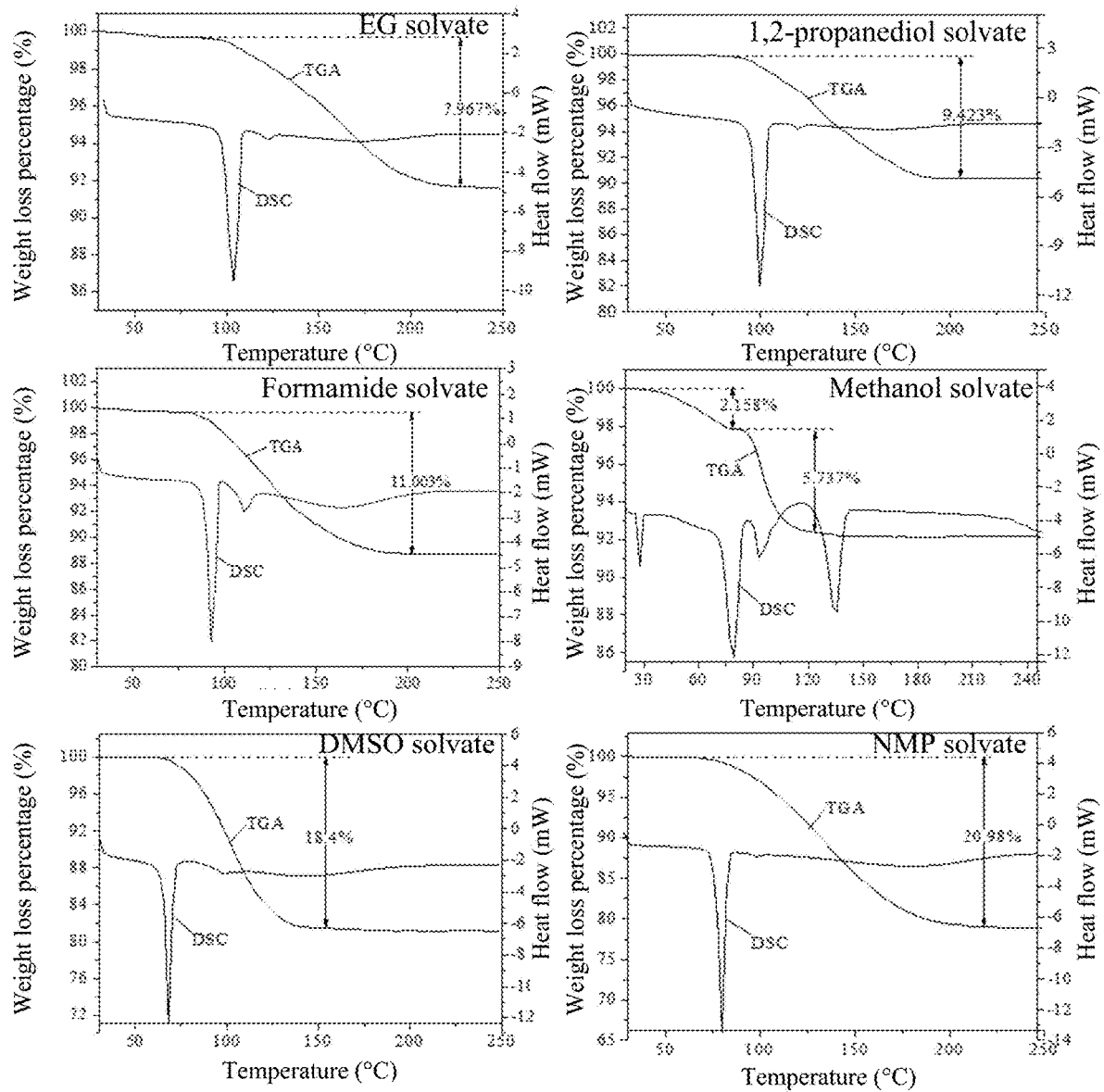
FIG. 3 shows thermal analysis charts of the 6 etoricoxib solvates.
Figure 4:
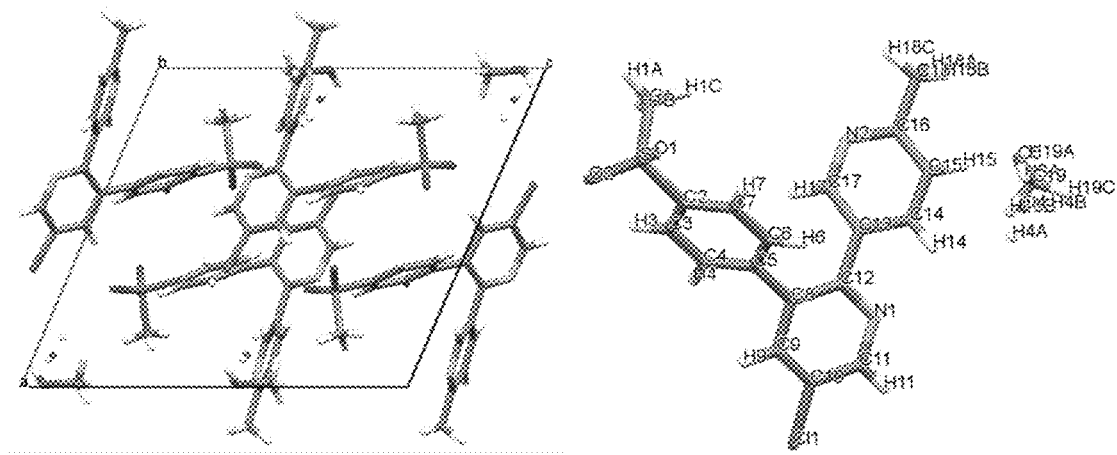
FIG. 4 (a) shows the molecular packing in a unit cell of the methanol solvate of etoricoxib, and FIG. 4 (b) shows the asymmetric unit structure of the methanol solvate of etoricoxib.
Figure 5:
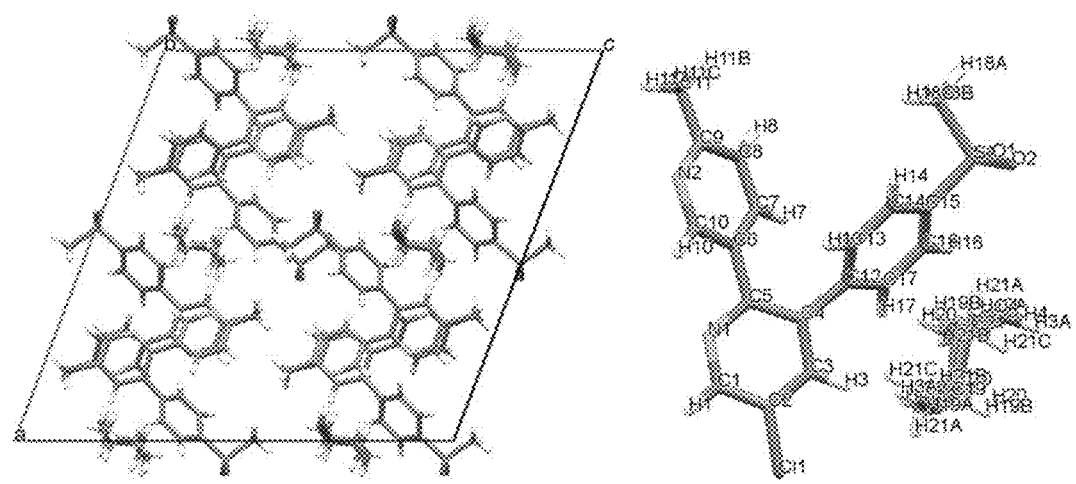
FIG. 5 (a) shows the molecular packing in a unit cell of the 1,2-propanediol solvate of etoricoxib, and FIG. 5 (b) shows the asymmetric unit structure of the 1,2-propanediol solvate of etoricoxib.
Figure 6:
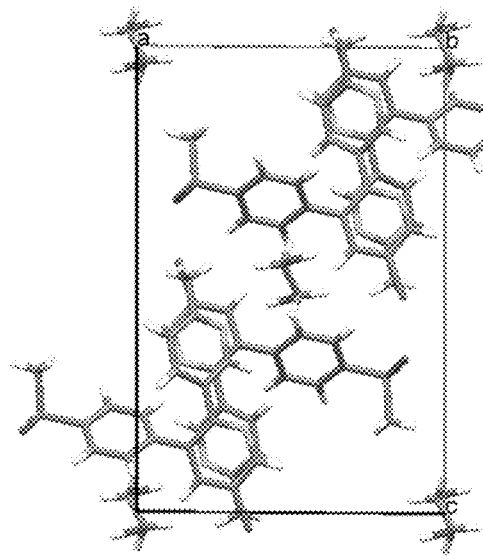
FIG. 6 (a) shows the molecular packing in a unit cell of the EG solvate of etoricoxib, and FIG. 6 (b) shows the asymmetric unit structure of the EG solvate of etoricoxib.
Figure 6:
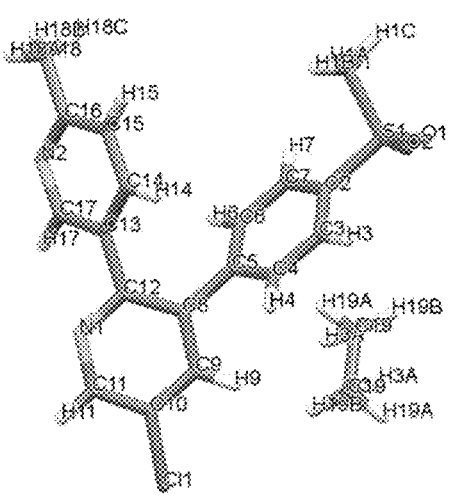
Figure 7:
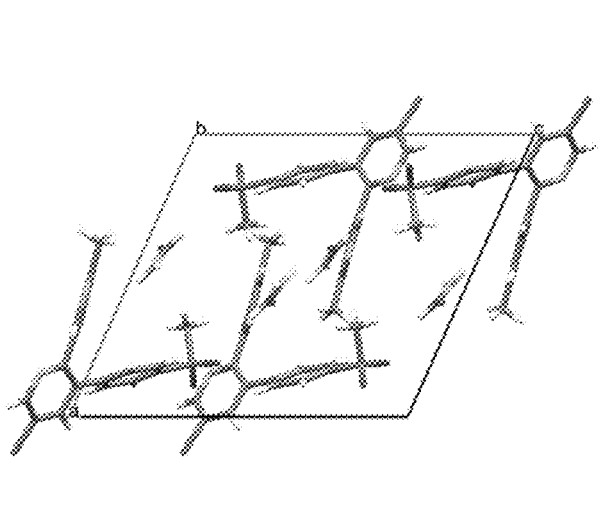
FIG. 7 (a) shows the molecular packing in a unit cell of the formamide solvate of etoricoxib, and FIG. 7 (b) shows the asymmetric unit structure of the formamide solvate of etoricoxib.
Figure 7:
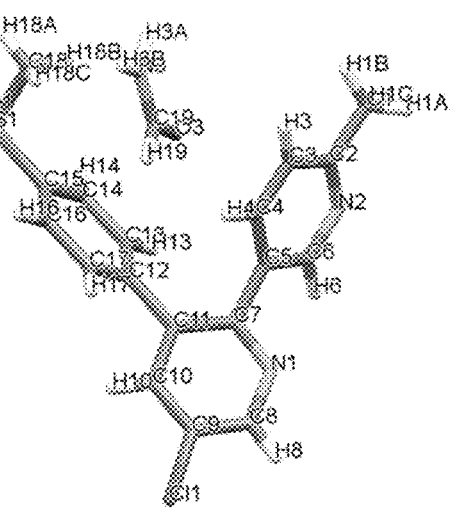
Figure 8:
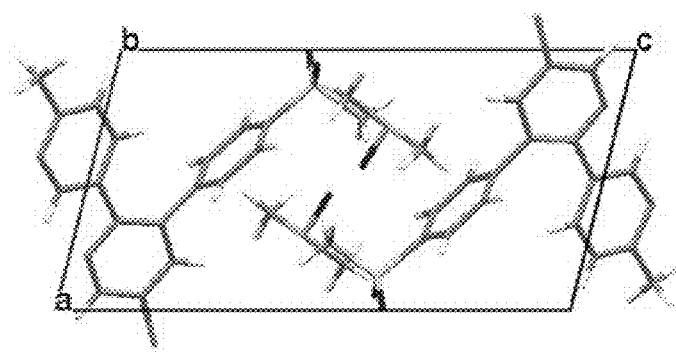
FIG. 8 (a) shows the molecular packing in a unit cell of the DMSO solvate of etoricoxib, and FIG. 8 (b) shows the asymmetric unit structure of the DMSO solvate of etoricoxib.
Figure 8:
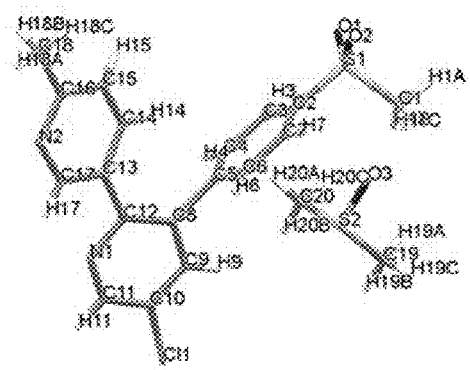
Figure 9:
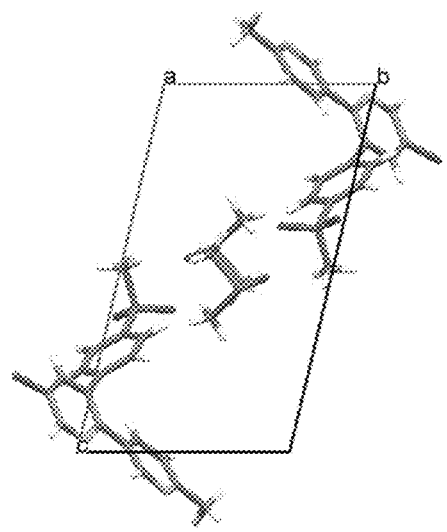
FIG. 9 (a) shows the molecular packing in a unit cell of the NMP solvate of etoricoxib, and FIG. 9 (b) shows the asymmetric unit structure of the NMP solvate of etoricoxib.
Figure 9:
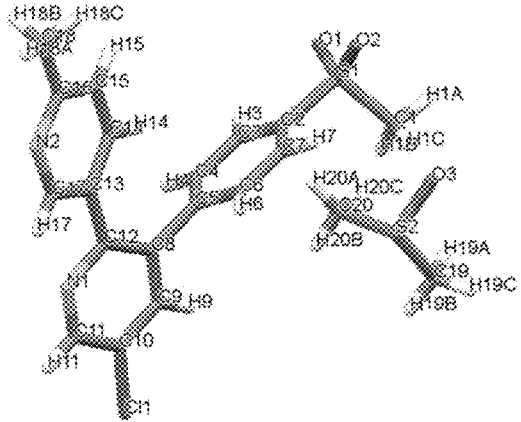
Figure 10:
FIG. 10 shows a microscope image of the 1,2-propanediol solvate of etoricoxib.
Figure 11:
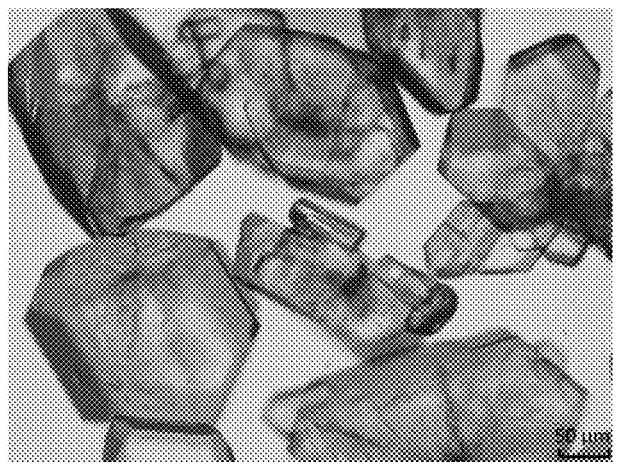
FIG. 11 shows a microscope image of the DMSO solvate of etoricoxib.

PXRD patterns of the obtained 6 etoricoxib solvates were shown in FIG. 2. Thermal analysis characteristics of the 6 etoricoxib solvates were shown in FIG. 3.

Example 2

Methanol with a polarity value $\pi^*=60$ was selected as a solvent from hydrogen bond donor solvents with a polarity value $\pi^*$ ranging from 60 to 100. The cooling crystallization was adopted. 3.58 g of an etoricoxib crystal form I sample was added to a crystallizer, then 3.2 g of methanol was added, and a resulting suspension was heated to 50° C. so that the sample was completely dissolved to obtain a clear solution, where, the etoricoxib and methanol had a molar ratio of 1:10; the clear solution was cooled to 10° C. at a cooling rate of 0.5° C./min and kept at the temperature for 1 h; then a resulting suspension was filtered; and an obtained filter cake was dried under vacuum at 20° C. for 8 h to obtain 3.71 g of a methanol solvate of etoricoxib, with a molar yield of 95.34%.

1 mol of the obtained methanol solvate of etoricoxib included 1 mol of methanol. The methanol solvate of etoricoxib belongs to monoclinic crystal system, P2/c space group with unit cell parameters of a=13.5993 Å, b=10.0612 Å, c=15.1833 Å, $\alpha=90°$, $\beta=113.50°$, and $\gamma=90°$, and unit cell volume of 1905.08 Å$^3$; in a PXRD pattern of the solvate, characteristic diffraction peaks appear at diffraction angles $2\theta(°)=7.08$, 11.48, 11.82, 14.28, 14.74, 15.46, 16.72, 17.24, 17.62, 18.74, 21.36, 21.78, 22.60, 23.10, 23.78, 24.48, 25.56, and 26.10; and according to a TG pattern of the solvate, desolvation starts at 27° C., with a weight loss of 8.0%.

Example 3

1,2-propanediol with a polarity value $\pi^*=85$ was selected as a solvent from hydrogen bond donor solvents with a polarity value $\pi^*$ ranging from 60 to 100. The cooling crystallization was adopted. 3.58 g of an etoricoxib crystal form II sample was added to 22.83 g of 1,2-propanediol, and a resulting suspension was heated to 65° C. so that the sample was completely dissolved to obtain a clear solution, where, the etoricoxib and 1,2-propanediol had a molar ratio of 1:30; the clear solution was cooled to 0° C. at a cooling rate of 1.25° C./min and kept at the temperature for 2.5 h;

then a resulting suspension was filtered; and an obtained filter cake was dried under vacuum at 60° C. for 8 h to obtain 3.66 g of a 1,2-propanediol solvate of etoricoxib, with a molar yield of 92.62%.

1 mol of the obtained 1,2-propanediol solvate of etoricoxib included 0.5 mol of 1,2-propanediol. The 1,2-propanediol solvate of etoricoxib belongs to monoclinic crystal system, C 2/c space group with unit cell parameters of a=21.731 Å, b=8.2933 Å, c=22.716 Å, α=90°, β=110.90°, and γ=90°, and unit cell volume of 3824.72 Å$^3$; in a PXRD pattern of the solvate, characteristic diffraction peaks appear at diffraction angles 2θ(°)=9.66, 11.70, 14.06, 15.84, 16.44, 17.46, 18.04, 23.14, 23.58, 24.10, 25.70, 26.06, 27.12, 29.02, 30.52, 32.96, 33.22, and 38.16; and according to a TG pattern of the solvate, desolvation starts at 94° C., with a weight loss of 9.4%.

Example 4

EG with a polarity value π*=92 was selected as a solvent from hydrogen bond donor solvents with a polarity value π* ranging from 60 to 100. The cooling crystallization was adopted. 3.58 g of an etoricoxib crystal form III sample was added to 12.41 g of EG, and a resulting suspension was heated to 80° C. so that the sample was completely dissolved to obtain a clear solution, where, the etoricoxib and EG had a molar ratio of 1:20; the clear solution was cooled to 20° C. at a cooling rate of 2° C./min and kept at the temperature for 5 h; then a resulting suspension was filtered; and an obtained filter cake was dried under vacuum at 50° C. for 8 h to obtain 3.63 g of an EG solvate of etoricoxib, with a molar yield of 93.33%.

1 mol of the obtained EG solvate of etoricoxib included 0.5 mol of EG. The EG solvate of etoricoxib belongs to monoclinic crystal system, P2$_1$/n space group with unit cell parameters of a=12.1502 Å, b=8.24082 Å, c=18.3654 Å, α=90°, β=90.45°, and γ=90°, and unit cell volume of 1838.76 Å$^3$; in a PXRD pattern of the solvate, characteristic diffraction peaks appear at diffraction angles 2θ(°)=9.62, 14.44, 16.16, 17.56, 19.50, 22.12, 22.45, 22.76, 23.30, 24.98, 26.04, 27.10, and 27.84; and according to a TG pattern of the solvate, desolvation starts at 96° C., with a weight loss of 8.0%.

Example 5

Formamide with a polarity value π*=97 was selected as a solvent from hydrogen bond donor solvents with a polarity value π* ranging from 60 to 100. The cooling crystallization was adopted. 3.58 g of an etoricoxib crystal form IV sample was added to 11.26 g of formamide, and a resulting suspension was heated to 70° C. so that the sample was completely dissolved to obtain a clear solution, where, the etoricoxib and formamide had a molar ratio of 1:25; the clear solution was cooled to 5° C. at a cooling rate of 1° C./min and kept at the temperature for 5 h; then a resulting suspension was filtered; and an obtained filter cake was dried under vacuum at 40° C. for 8 h to obtain 3.93 g of a formamide solvate of etoricoxib, with a molar yield of 97.53%.

1 mol of the obtained formamide solvate of etoricoxib included 1 mol of formamide. The formamide solvate of etoricoxib belongs to monoclinic crystal system, P2/c space group with unit cell parameters of a=13.6203 Å, b=10.4282 Å, c=14.8913 Å, α=90°, β=114.11°, and γ=90°, and unit cell volume of 1930.58 Å$^3$; in a PXRD pattern of the solvate, characteristic diffraction peaks appear at diffraction angles 2θ(°)=11.26, 13.02, 14.24, 14.72, 15.56, 16.58, 17.00, 17.18, 18.20, 18.44, 19.22, 19.86, 20.52, 22.64, 22.98, 24.28, 25.62, 26.04, 26.20, 27.58, 28.70, 29.68, and 30.28; and according to a TG pattern of the solvate, desolvation starts at 90° C., with a weight loss of 11.0%.

Example 6

DMSO with a polarity value π*=100 was selected as a solvent from hydrogen bond acceptor solvents with a polarity value π* ranging from 92 to 100. The cooling crystallization was adopted. 3.58 g of an etoricoxib amorphous form sample was added to 11.72 g of DMSO, and a resulting suspension was heated to 55° C. so that the sample was completely dissolved to obtain a clear solution, where, the etoricoxib and DMSO had a molar ratio of 1:15; the clear solution was cooled to 18° C. at a cooling rate of 1.5° C./min and kept at the temperature for 3 h; then a resulting suspension was filtered; and an obtained filter cake was dried under vacuum at 40° C. for 8 h to obtain 4.18 g of a DMSO solvate of etoricoxib, with a molar yield of 95.88%.

1 mol of the obtained DMSO solvate of etoricoxib included 1 mol of DMSO. The DMSO solvate of etoricoxib belongs to triclinic crystal system, P-1 space group with unit cell parameters of a=8.3464(17) Å, b=8.8665(18) Å, c=15.210(3) Å, α=99.04°, β=100.16°, and γ=108.93°, and unit cell volume of 1019.87 Å$^3$; in a PXRD pattern of the solvate, characteristic diffraction peaks appear at diffraction angles 2θ(°)=10.87, 12.14, 12.66, 14.58, 17.34, 17.80, 18.08, 19.08, 21.13, 22.00, 22.28, 23.44, 24.24, 25.00, 25.46, 26.14, 29.42, and 30.38; and according to a TG pattern of the solvate, desolvation starts at 66° C., with a weight loss of 18.4%.

Example 7

NMP with a polarity value π*=92 was selected as a solvent from hydrogen bond acceptor solvents with a polarity value π* ranging from 92 to 100. The cooling crystallization was adopted. 3.67 g of an etoricoxib hemihydrate sample was added to 9.91 g of NMP, and a resulting suspension was heated to 60° C. so that the sample was completely dissolved to obtain a clear solution, where, the etoricoxib and NMP had a molar ratio of 1:10; the clear solution was cooled to 15° C. at a cooling rate of 1.8° C./min and kept at the temperature for 4 h; then a resulting suspension was filtered; and an obtained filter cake was dried under vacuum at 30° C. for 8 h to obtain 4.46 g of an NMP solvate of etoricoxib, with a molar yield of 97.61%.

1 mol of the obtained NMP solvate of etoricoxib included 1 mol of NMP. The NMP solvate of etoricoxib belongs to triclinic crystal system, P-1 space group, with unit cell parameters of a=9.0649(18)Å, b=10.924(2)Å, c=11.964(2) Å, α=76.38°, β=84.23° and γ=79.82°, and unit cell volume of 1131.24 Å$^3$; in a PXRD pattern of the solvate, characteristic diffraction peaks appear at diffraction angles 2θ(°) =8.42, 10.02, 15.26, 15.72, 16.92, 17.98, 18.22, 19.04, 19.92, 20.38, 20.80, 21.80, 22.88, 23.68, 24.06, 24.36, 24.90, and 25.74; and according to a TG pattern of the solvate, desolvation starts at 79° C., with a weight loss of 21.0%.

Example 8

Methanol with a polarity value π*=60 was selected as a solvent from hydrogen bond donor solvents with a polarity value π* ranging from 60 to 100. The suspension crystallization was adopted. 3.58 g of an etoricoxib crystal form I sample was added to 4.81 g of methanol to obtain a suspension, where, the etoricoxib and methanol had a molar ratio of 1:15; the suspension was stirred at 20° C. for 2 h; after the stirring was completed, a resulting suspension was filtered; and an obtained filter cake was dried under vacuum at 20° C. for 8 h to obtain 3.63 g of a methanol solvate of etoricoxib, with a molar yield of 93.30%.

1 mol of the obtained methanol solvate of etoricoxib included 1 mol of methanol. The methanol solvate of etoricoxib belongs to monoclinic crystal system, P2/c space group with unit cell parameters of a=13.5993 Å, b=10.0612 Å, c=15.1833 Å, α=90°, β=113.50°, and γ=90°, and unit cell volume of 1905.08 Å$^3$; in a PXRD pattern of the solvate, characteristic diffraction peaks appear at diffraction angles 2θ(°)=7.08, 11.48, 11.82, 14.28, 14.74, 15.46, 16.72, 17.24, 17.62, 18.74, 21.36, 21.78, 22.60, 23.10, 23.78, 24.48, 25.56, and 26.10; and according to a TG pattern of the solvate, desolvation starts at 27° C., with a weight loss of 8.0%.

Example 9

1,2-propanediol with a polarity value π*=85 was selected as a solvent from hydrogen bond donor solvents with a polarity value π* ranging from 60 to 100. The suspension crystallization was adopted. 3.58 g of an etoricoxib crystal form II sample was added to 19.02 g of 1,2-propanediol to obtain a suspension, where, the etoricoxib and 1,2-propanediol had a molar ratio of 1:25; the suspension was stirred at 30° C. for 4 h; after the stirring was completed, a resulting suspension was filtered; and an obtained filter cake was dried under vacuum at 60° C. for 8 h to obtain 3.71 g of a 1,2-propanediol solvate of etoricoxib, with a molar yield of 93.70%.

1 mol of the obtained 1,2-propanediol solvate of etoricoxib included 0.5 mol of 1,2-propanediol. The 1,2-propanediol solvate of etoricoxib belongs to monoclinic crystal system, C 2/c space group with unit cell parameters of a=21.731 Å, b=8.2933 Å, c=22.716 Å, α=90°, β=110.90°, and γ=90°, and unit cell volume of 3824.72 Å$^3$; in a PXRD pattern of the solvate, characteristic diffraction peaks appear at diffraction angles 2θ(°)=9.66, 11.70, 14.06, 15.84, 16.44, 17.46, 18.04, 23.14, 23.58, 24.10, 25.70, 26.06, 27.12, 29.02, 30.52, 32.96, 33.22, and 38.16; and according to a TG pattern of the solvate, desolvation starts at 94° C., with a weight loss of 9.4%.

Example 10

EG with a polarity value π*=92 was selected as a solvent from hydrogen bond donor solvents with a polarity value π* ranging from 60 to 100. The suspension crystallization was adopted. 3.58 g of an etoricoxib crystal form III sample was added to 12.41 g of EG to obtain a suspension, where, the etoricoxib and EG had a molar ratio of 1:20; the suspension was stirred at 35° C. for 5 h; after the stirring was completed, a resulting suspension was filtered; and an obtained filter cake was dried under vacuum at 50° C. for 8 h to obtain 3.54 g of an EG solvate of etoricoxib, with a molar yield of 91.01%.

1 mol of the obtained EG solvate of etoricoxib included 0.5 mol of EG. The EG solvate of etoricoxib belongs to monoclinic crystal system, P2$_1$/n space group with unit cell parameters of a=12.1502 Å, b=8.24082 Å, c=18.3654 Å, α=90°, β=90.45°, and γ=90°, and unit cell volume of 1838.76 Å$^3$; in a PXRD pattern of the solvate, characteristic diffraction peaks appear at diffraction angles 2θ(°)=9.62, 14.44, 16.16, 17.56, 19.50, 22.12, 22.45, 22.76, 23.30, 24.98, 26.04, 27.10, and 27.84; and according to a TG pattern of the solvate, desolvation starts at 96° C., with a weight loss of 8.0%.

Example 11

Formamide with a polarity value π*=97 was selected as a solvent from hydrogen bond donor solvents with a polarity value π* ranging from 60 to 100. The suspension crystallization was adopted. 3.58 g of an etoricoxib crystal form IV sample was added to 13.51 g of formamide to obtain a suspension, where, the etoricoxib and formamide had a molar ratio of 1:30; the suspension was stirred at 40° C. for 5 h; after the stirring was completed, a resulting suspension was filtered; and an obtained filter cake was dried under vacuum at 40° C. for 8 h to obtain 3.72 g of a formamide solvate of etoricoxib, with a molar yield of 92.32%.

1 mol of the obtained formamide solvate of etoricoxib included 1 mol of formamide. The formamide solvate of etoricoxib belongs to monoclinic crystal system, P2/c space group with unit cell parameters of a=13.6203 Å, b=10.4282 Å, c=14.8913 Å, α=90°, β=114.11°, and γ=90°, and unit cell volume of 1930.58 Å$^3$; in a PXRD pattern of the solvate, characteristic diffraction peaks appear at diffraction angles 2θ(°)=11.26, 13.02, 14.24, 14.72, 15.56, 16.58, 17.00, 17.18, 18.20, 18.44, 19.22, 19.86, 20.52, 22.64, 22.98, 24.28, 25.62, 26.04, 26.20, 27.58, 28.70, 29.68, and 30.28; and according to a TG pattern of the solvate, desolvation starts at 90° C., with a weight loss of 11.0%.

Example 12

DMSO with a polarity value π*=100 was selected as a solvent from hydrogen bond acceptor solvents with a polarity value π* ranging from 92 to 100. The suspension crystallization was adopted. 3.58 g of an etoricoxib crystal form V sample was added to 7.81 g of DMSO to obtain a suspension, where, the etoricoxib and DMSO had a molar ratio of 1:10; the suspension was stirred at 27.5° C. for 1 h; after the stirring was completed, a resulting suspension was filtered; and an obtained filter cake was dried under vacuum at 40° C. for 8 h to obtain 3.97 g of a DMSO solvate of etoricoxib, with a molar yield of 91.07%.

1 mol of the obtained DMSO solvate of etoricoxib included 1 mol of DMSO. The DMSO solvate of etoricoxib belongs to triclinic crystal system, P-1 space group with unit cell parameters of a=8.3464(17) Å, b=8.8665(18) Å, c=15.210(3) Å, α=99.04°, β=100.16°, and γ=108.93°, and unit cell volume of 1019.87 Å$^3$; in a PXRD pattern of the solvate, characteristic diffraction peaks appear at diffraction angles 2θ(°)=10.87, 12.14, 12.66, 14.58, 17.34, 17.80, 18.08, 19.08, 21.13, 22.00, 22.28, 23.44, 24.24, 25.00, 25.46, 26.14, 29.42, and 30.38; and according to a TG pattern of the solvate, desolvation starts at 66° C., with a weight loss of 18.4%.

Example 13

NMP with a polarity value π*=92 was selected as a solvent from hydrogen bond acceptor solvents with a polarity value π* ranging from 92 to 100. The suspension crystallization was adopted. 3.58 g of a mixture of etoricoxib crystal forms I, II, III, IV, and V was added to 19.83 g of NMP to obtain a suspension, where, the etoricoxib and NMP had a molar ratio of 1:20; the suspension was stirred at 15° C. for 3 h; after the stirring was completed, a resulting suspension was filtered; and an obtained filter cake was dried under vacuum at 30° C. for 8 h to obtain 4.25 g of an NMP solvate of etoricoxib, with a molar yield of 93.02%.

1 mol of the obtained NMP solvate of etoricoxib included 1 mol of NMP. The NMP solvate of etoricoxib belongs to triclinic crystal system, P-1 space group, with unit cell parameters of a=9.0649(18)Å, b=10.924(2)Å, c=11.964(2) Å, α=76.38°, β=84.23° and γ=79.82°, and unit cell volume of 1131.24 Å$^3$; in a PXRD pattern of the solvate, characteristic diffraction peaks appear at diffraction angles 2θ(°) =8.42, 10.02, 15.26, 15.72, 16.92, 17.98, 18.22, 19.04, 19.92, 20.38, 20.80, 21.80, 22.88, 23.68, 24.06, 24.36, 24.90, and 25.74; and according to a TG pattern of the solvate, desolvation starts at 79° C., with a weight loss of 21.0%.

Those skilled in the art can appropriately change the conditions and routes with reference to the content of this specification to implement the technical solutions disclosed and proposed in the present disclosure. Although the method and preparation technology of the present disclosure have been described through preferred examples, the relevant technical personnel apparently can modify or recombine the methods and technical routes described herein without departing from the content, spirit and scope of the present disclosure to realize the final preparation technology. In particular, it should be noted that all similar replacements and modifications are obvious to those skilled in the art, and the replacements and modifications are all deemed to be included in the spirit, scope and content of the present disclosure.

What is claimed is:

1. Etoricoxib solvate comprising dimethyl sulfoxide (DMSO) solvate of etoricoxib, wherein 1 mol of the DMSO solvate of etoricoxib comprises 1 mol of DMSO, and the DMSO solvate of etoricoxib belongs to triclinic crystal system, P-1 space group with unit cell parameters of a=8.3464(17) Å, b=8.8665(18) Å, c=15.210(3) Å, α=99.04°, β=100.16°, and γ=108.93°; in a PXRD pattern of the solvate, characteristic diffraction peaks appear at diffraction angles 2θ(°)=10.87±0.1, 12.14±0.1, 12.66±0.1, 14.58±0.1, 17.34±0.1, 17.80±0.1, 18.08±0.1, 19.08±0.1, 21.13±0.1, 22.00±0.1, 22.28±0.1, 23.44±0.1, 24.24±0.1, 25.00±0.1, 25.46±0.1, 26.14±0.1, 29.42±0.1, and 30.38±0.1; and according to a TG pattern of the solvate, desolvation starts at 66±1° C., with a weight loss of 18.4%.

2. A method of making the etoricoxib solvate according to claim 1, wherein, cooling crystallization is adopted, and the method comprises the following steps:
   (1) adding a raw material of etoricoxib to a solvent, and heating a resulting suspension to 50° C. to 80° C. to obtain a clear solution, wherein, the etoricoxib and the solvent have a molar ratio of 1:10 to 1:30, and the solvent is DMSO;
   (2) cooling the clear solution to 0° C. to 20° C. at a cooling rate of 0.5° C./min to 2° C./min and holding the temperature for 1 h to 5 h; and
   (3) filtering a resulting suspension to obtain a filter cake after the cooling crystallization is completed, and drying the filter cake under vacuum at 20° C. to 60° C. to obtain the etoricoxib solvate.

3. A method of making the etoricoxib solvate according to claim 1, wherein, suspension crystallization is adopted, and the method comprises the following steps:
   (1) adding a raw material of etoricoxib to a solvent to obtain a suspension, wherein, the etoricoxib and the solvent have a molar ratio of 1:10 to 1:30, and the solvent is DMSO;
   (2) stirring the suspension at a constant temperature of 15° C. to 40° C. for 1 h to 5 h; and
   (3) filtering a resulting suspension to obtain a filter cake after the stirring is completed, and drying the filter cake under vacuum at 20° C. to 60° C. to obtain the etoricoxib solvate.

4. The preparation method of the etoricoxib solvate according to claim 2, wherein, the raw material of etoricoxib is one of etoricoxib amorphous form, crystal form I, crystal form II, crystal form III, crystal form IV, crystal form V, and hemihydrate, or a mixture of two or more thereof.

5. The method according to claim 3, wherein, the raw material of etoricoxib is one of etoricoxib amorphous form, crystal form I, crystal form II, crystal form III, crystal form IV, crystal form V, and hemihydrate, or a mixture of two or more thereof.

* * * * *